United States Patent [19]
Forat et al.

[11] Patent Number: 5,756,849
[45] Date of Patent: May 26, 1998

[54] PROCESS FOR GRAFTING A SUBSTITUTED DIFLUOROMETHYL GROUP ONTO A COMPOUND CONTAINING AN ELECTROPHILIC FUNCTIONAL GROUP

[75] Inventors: Gérard Forat, Lyons; Jean-Manuel Mas, Millery; Laurent Saint-Jalmes, Meyzieu, all of France

[73] Assignee: Rhone-Poulenc Chimie, Courbevoie Cedex, France

[21] Appl. No.: 620,348

[22] Filed: Mar. 22, 1996

[30] Foreign Application Priority Data

Mar. 24, 1995 [FR] France .................................. 95 03512
Dec. 29, 1995 [FR] France .................................. 95 15763

[51] Int. Cl.$^6$ .................... C07C 29/38; C07C 315/00; C07C 319/14
[52] U.S. Cl. .................... 568/27; 562/493; 562/605; 568/28; 568/56; 568/44; 568/812; 568/835; 568/842
[58] Field of Search .................... 562/605; 568/27, 568/35, 56

[56] References Cited

U.S. PATENT DOCUMENTS 4,808,748  2/1989  Lin et al. .................................. 558/378
4,990,699  2/1991  Stahly .................................. 568/933

FOREIGN PATENT DOCUMENTS 0307519  3/1989  European Pat. Off. .

OTHER PUBLICATIONS

Journal of Fluorine Chemistry, vol. 45, No. 3, Dec. 1989, Lausanne, CH, pp. 431–433, G.P. Stahly: 'Trifluoromethylation of 1,3,5-Trinitrobenzene.'

Journal of the Chemical Society, Perkin Transactions 1, No. 7, Jul. 1990, Letchworth, GB, pp. 1951–1957, M. Tordeux, et al.: 'Reactions of trifluoromethyl bromide and related halides: part 9. Comparison between additions to carbonyl compounds, enamines, and sulfur dioxide in the presence of zinc.'

Primary Examiner—Michael G. Ambrose
Attorney, Agent, or Firm—Burns, Doane, Swecker & Mathis, L.L.P.

[57] ABSTRACT

The invention relates to a process and a nucleophilic reagent which is useful for grafting a substituted difluoromethyl group onto a compound containing at least one electrophilic function, characterized in that it comprises:
  a) a fluorocarboxylic acid of formula Ew—$CF_2$—COOH where Ew represents an electron-withdrawing atom or group, at least partially salified with an organic or inorganic cation, and
  b) a polar aprotic solvent;

and in that the content of releasable protons carried by its various components, including their impurities, is at most equal to half the initial molar concentration of the said fluorocarboxylic acid.

20 Claims, No Drawings

PROCESS FOR GRAFTING A SUBSTITUTED DIFLUOROMETHYL GROUP ONTO A COMPOUND CONTAINING AN ELECTROPHILIC FUNCTIONAL GROUP

The present invention relates to a reagent and a process for grafting a substituted difluoromethyl group onto a compound containing at least one electrophilic function. The invention relates more particularly to a technique for perfluoroalkylating various compounds by nucleophilic substitution reactions or addition reactions typically performed by organometallic derivatives.

The techniques of perfluoroalkylation, or equivalent techniques, generally use derivatives of the perfluoroalkyl iodide type, in the presence of zinc. This technique is thus expensive, while at the same time requiring treatment plants for the metallic waste which should be treated, since zinc is a great pollutant of water courses.

The other techniques, in which the perfluoroalkyl radical does not form a stabilized reactive intermediate of the organometallic type, are generally difficult to carry out on account of the very low stability of the free perfluoro anions in the reaction media. These anions generally lead to products of the carbene type, by loss of one of their substituents.

Consequently, one of the aims of the present invention is to provide a reagent which allows a perfluoroalkylation according to a mechanism of the type involving a carbanion, without using organometallic reagents of transition metals such as zinc.

It has often been sought to use as a source of perfluoroalkyl radicals, more generally of trifluoromethyl radicals, perfluorocarboxylic acids, by carrying out decomposition reactions aimed at eliminating the carboxylic fragment from the said acids, releasing carbon dioxide. However, the successes which were obtained were very mitigated and used particularly complex catalytic systems. The perfluoroalkyl radicals or equivalents thereof generated by the decomposition of the said perfluorocarboxylic acids were, in addition, unstable in the reaction medium and required the use of stabilizing agents.

G. Stahly has also reported, in Journal of Fluorine Chemistry, 45 (1989), 431–433 and in U.S. Pat. No. 4,990,699, that the thermal decomposition of perfluoroalkanoic salts in the presence of aromatic compounds such as 1,3,5-trinitrobenzene leads to the formation of trifluoromethyl anions $CF_3^-$, demonstrated by the formation of a Meisenheimer complex. The complex may subsequently be converted by oxidation to give the perfluoroalkyl derivative on the corresponding aromatic ring.

However, the need to carry out this oxidation makes this route for the perfluoroalkylation of aromatic derivatives tedious.

The present invention proposes to circumvent the drawbacks of the existing processes by providing a reagent which is non-hazardous to the environment and capable of leading to the desired products in a satisfactory yield.

In the course of the study which led to the present invention, it has been demonstrated that a fluoroalkylation reaction was possible with a fluorocarboxylic acid salt, without a catalyst and without an agent capable of stabilizing the various envisaged intermediates obtained during the decomposition of the various perfluorocarboxylic acids.

It appeared that, in order thus to obtain a decomposition of the fluorocarboxylic acids, two conditions were essential; one is the choice of the solvent, and the other the content of impurities in the mixture constituting the reagent according to the present invention. Thus, it was possible to demonstrate the absolutely critical role of the content of labile hydrogens in the system, or more precisely of releasable protons, which must be less than the content of fluoro groups released by the decomposition of the fluorocarboxylic acid salts. The terms labile hydrogen and releasable proton refer to a hydrogen atom which is capable of being removed out in the form of a proton by a strong base. In practice, these are protons of acidic functions which have a pKa of less than about 20 (by "about", it is emphasized that the number 20 has only one significant figure).

The abovementioned aims and others, which will appear later, are achieved by means of a nucleophilic reagent which is useful for grafting a substituted difluoromethyl group onto a compound containing at least one electrophilic function, characterized in that it comprises:

a) a fluorocarboxylic acid of formula Ew—$CF_2$—COOH where Ew represents an electron-withdrawing atom or group, at least partially salified with an organic or inorganic cation, and b) a polar aprotic solvent;

and in that the content of releasable protons carried by its various components, including their impurities, is at most equal to half the initial molar concentration of the said fluorocarboxylic acid.

The electrophilic functions capable of reacting with the reagent of the present invention are the functions which usually react with organometallic reagents and will be detailed later.

The lower the content of releasable protons in the reagent, the lower the risk of side reactions will be and the better the yield will be.

Thus, it is preferable for the content of labile hydrogen atoms in the reagent to be at most equal to 10%, preferably to 1% (in moles), relative to the initial content of the said fluorocarboxylic acid.

The main impurity, as a carrier of labile hydrogen atoms, is generally water, which is capable of releasing up to two hydrogen atoms per molecule.

In general, it is preferable to use carefully dehydrated reagents and solvents, so that the weight content of water in the reagent is at most equal to 1 per 1000 relative to the total mass of the reagent.

Depending on the overall reaction conditions, such water contents may be satisfactory, but in certain cases, it may be advantageous to work at lower levels, for example of about 1 per 10,000.

However, it is not necessarily essential to remove all of the water and a water/fluorocarboxylic acid molar ratio of less than 10% may be tolerated.

Moreover, it was possible to show that other elements, namely transition elements having two stable valency states, such as copper, may not be beneficial, and could even be harmful.

Although this reagent according to the invention requires no catalyst, such metal elements may be present as impurities supplied in particular by the solvent.

Thus, it is preferable for the molar content of these elements to be less than 1000, advantageously than 100, and preferably than 10 ppm relative to the initial content of the said fluorocarboxylic acid.

Also, although it has been recommended many times to use elements from column VIII of the Periodic Table of the Elements with perfluoroacetic acid, in order to promote certain substrates and to promote certain types of reaction, this proved to be particularly harmful for the reaction intended above. Consequently, it is preferable to use reagents containing no metals from column VIII, in particular metals of the platinum ore, which is the group consisting of platinum, osmium, iridium, palladium, rhodium and ruthenium.

In the present description, reference is made to the supplement to the Bulletin de la Société Chimique de France No. 1, January 1966, in which a Periodic Table of the Elements was published.

Thus, it is preferable for the content of platinum ore metals, or even of metals from column VIII, to be less than 100 ppm, advantageously than 10 ppm, preferably than 1 ppm. These values are expressed relative to the starting fluorocarboxylic acid and are expressed in moles.

In a more general and more empirical manner, it may be indicated that these two categories of metals, namely transition metals with two valency states and the elements of column VIII, should be present in the reagent at an overall concentration level at most equal to 1000 mol ppm, preferably to 10 mol ppm.

It will be noted that the various metals present at such an overall concentration level are extremely low in quantity and, in this respect, they play no catalytic role. Their presence does not improve the reaction kinetics, or is even harmful thereto when they are present in too large an amount.

The use, in addition to the components of the abovementioned reagents, of alkali metal fluoride or of quaternary ammonium fluoride, which are usually present in the reagent systems using fluorocarboxylates, did not turn out to be harmful, but did prove to be of little value, on account of the fact that it produces saline effluents which are difficult to treat.

It is noted, however, that the presence of fluorides in the medium tends to limit the conversion of the fluorocarboxylic acid, but tends to reduce side reactions.

This effect tends to be greater the bulkier the countercation of the fluoride. Cations which may be envisaged are the cations of alkali metals higher in rank than sodium, in particular potassium or caesium, or alternatively ions of "onium" type, namely cations formed by the elements of columns V B and VI B (as defined in the Periodic Table of the Elements published in the supplement to the Bulletin de la Société Chimique de France in January 1966), with 4 or 3 hydrocarbon chains.

Among the oniums derived from elements of column V B, the preferred reagents are tetraalkyl or tetraaryl ammonium or phosphonium. The hydrocarbon group advantageously contains from 4 to 12 carbon atoms, preferably from 4 to 8 carbon atoms. The oniums derived from column VI B are preferably derived from elements with an atomic number higher than that of oxygen.

Despite the drawbacks which have been mentioned above, the content of fluoride ions is a parameter which may be considered. It may, however, be preferable to limit this content, in particular the initial content, so as to facilitate the final treatment of the reaction medium.

Thus, it is advantageous for the content of fluoride, which is qualified as being ionic, that is to say capable of being ionized in the polarizing medium of the reagent, to be at least equal to the initial molar concentration of the said fluorocarboxylic acid salt, advantageously to a half and preferably to a quarter of this concentration.

As has been mentioned above, the solvent plays an important role in the present invention and must be aprotic and advantageously polar and contain very few impurities carrying acidic hydrogen.

It is thus preferable for the polar aprotic solvent which can be used to have a significant dipolar moment. Thus, its relative dielectric constant $\epsilon$ is advantageously at least equal to about 5 (the positional zeros are not considered as being significant figures in the present description unless specified otherwise). Preferably, $\epsilon$ is less than or equal to 50 and greater than or equal to 5, and is in particular between 30 and 40.

It is moreover preferred for the solvents of the invention to be capable of fully solvating the cations, which may be classified by the donor number DN of these solvents. It is thus preferable for the donor number DN of these solvents to be between 10 and 30. The said donor number corresponds to the $\Delta H$ (enthalpy difference), expressed in kilocalories per mole, for the association of the said polar aprotic solvent with antimony pentachloride.

According to the present invention, it is preferable for the reagent to have no acidic hydrogen on the polar solvent or solvents which it uses. In particular, when the polar nature of the solvent or solvents is obtained by the presence of electron-withdrawing groups, it is desirable for there to be no hydrogen alpha to the electron-withdrawing function.

More generally, as for all the components of the reagents, it is preferable for the pKa corresponding to the first acidity of the solvent to be at least equal to about 20 ("about" emphasizing that only the first figure is significant), advantageously at least equal to about 25, preferably between 25 and 35.

The acidic nature may also be expressed by the acceptor number AN of the solvent, as defined by Reichardt in "Solvents and solvent effects in Organic Chemistry", 2nd edition, VCH (RFA), 1990, pages 23–24. Advantageously, this acceptor number AN is less than 20, in particular less than 18.

It is preferable for the said fluorocarboxylic acid or acid salt to be at least partially (at least 10 mol %), preferably fully, soluble in the medium constituting the reagent.

The solvents which give good results may in particular be solvents of amide type. Among the amides, amides of specific nature are also included, such as tetrasubstituted ureas including cyclic tetrasubstituted ureas, in particular 5- or 6-membered ureas, for example DMPU (dimethylpropylenylurea or 1,3-dimethyl-3,4,5,6-tetrahydro-2(1H)pyrimidinone) and DMEU (dimethylethylenylurea), or 1,3-dimethyl-2-imidazolidinone and monosubstituted lactams. The amides are preferably substituted (disubstituted for ordinary amides). Examples which may be mentioned are pyrrolidone derivatives, such as N-methylpyrrolidone, or alternatively N,N-dimethylformamide or N,N-dimethylacetamide.

Solvents such as 1,3-dimethyl-3,4,5,6-tetrahydro-2(1H) pyrimidinone (DMPU) or benzonitrile are also advantageous.

Another particularly advantageous category of solvents consists of ethers, whether these are symmetrical or unsymmetrical ethers and whether or not they are open. The various glycol ether derivatives such as the various glymes, for example diglyme, should also be incorporated into the category of ethers.

In the fluorocarboxylic acid of the constituent a) of the reagent of the invention, the species Ew which exerts an electron-withdrawing effect on the difluoro carbon atom is preferably selected from functional groups whose Hammett constant $\sigma_p$ is at least equal to 0.1. It is moreover preferable for the inductive component of $\sigma_p$, $\sigma_i$, to be at least equal to 0.2, advantageously to 0.3. In this respect, reference will be made to the book by March, "Advanced Organic Chemistry", third edition, John Wiley and Son, pages 242 to 250, and in particular to Table 4 of this section.

More particularly, the electron-withdrawing species may be selected from halogen atoms, preferably light ones, in particular chlorine and fluorine. The corresponding fluorocarboxylic acid is a halofluoroacetic acid of formula (1) X—$CF_2$—COOH where X is a halogen atom, advantageously a light one (chlorine or fluorine).

Ew may also be advantageously selected from nitrile (with the risk, as a side reaction, of an α-elimination), carbonylated, sulphonated, and perfluoroalkylated groups. Fluorocarboxylic acids of this type which may be used correspond to the formula (2) R—G—$CF_2$—COOH where R—G represents a nitrile group or alternatively G represents >C=O,>S=O, or —$(CF_2)n$— where n is greater than or equal to 1, and R represents, without discrimination, an organic or even an inorganic residue, preferably an organic radical such as aryl, alkyl or aralkyl, which is optionally substituted. R may also represent an organic solid support, such as a resin, or an inorganic solid support.

In the case where G represents a perfluoroalkylene group —$(CF_2)_n$—, n is advantageously between 1 and 10, preferably between 1 and 5. Still in this case, R may also represent a halogen atom, in particular fluorine.

In general, except in the case where the fluorocarboxylic acid is a polymer, the total number of carbon atoms in the fluorocarboxylic acid advantageously does not exceed 50.

The counter-cations capable of forming a salt with the said fluorocarboxylic acid are advantageously bulky. Thus, alkali metal salts, advantageously those in which the alkali metal is selected from sodium, potassium, rubidium, caesium or francium, are preferred. Preferably, the said metal is from a period at least equal in rank to that of sodium, advantageously to that of potassium. Quaternary ammonium salts are also preferred.

It is also possible to improve the reaction by using cations which are either naturally bulky, such as quaternary ammonium cations or quaternary phosphonium cations, or which are rendered bulky by the addition of chelating agents or preferably cryptands, such as, for example, crown ethers or derivatives which are both aminated and oxygenated.

The chelating or sequestering agents which may thus be used are advantageously selected on the one hand, from amines and, on the other hand, from ethers whose molecules contain at least one other ether function.

Thus, the sequestering agents which may be used are advantageously selected such that they contain either at least one amine function, or alternatively an ether function and at least one amine and/or ether function in order to form a completing agent which is advantageously at least bidentate, preferably tridentate, the ether and/or amine functions being separated by at least 1 atom, advantageously 2 atoms and by not more than 4 atoms, advantageously not more than 3 atoms, these generally being carbon atoms.

When the carbon atoms supposed to provide the coordination are connected together by 2 branches thus forming a ring, it is preferable for at least one branch to be at least 3-membered, advantageously 4-membered, and for the other branch to be at least 2-membered, advantageously 3-membered.

The bulk and the mobility should be such that the bi-, tri- or polydentate agents are complexing. Such is not the case with 1,4-diazabicyclo(2.2.2.)octane.

In general, this constraint may be quantified by showing that the bicyclic systems obtained by bridging of a ring (which are in fact tricyclic), and which are at most 8-membered, especially when the bridgeheads are the atoms providing the coordination, of the diazabicyclooctane, , -heptane and lower type and, to a lesser extent, -nonane, should be avoided.

More generally, it is advantageous to avoid any bicyclic system:

whose bridgeheads are atoms intended to provide the coordination and 2 branches of which have, not taking the bridgeheads into account, a chain length of not more than 2, preferably of not more than 3 when the third branch is less than 7-membered in length.

The at least bidentate nature with preferably at least one amine function is necessary for phosgene and derivatives, but not for oxalyl halide and equivalents.

At least 3 classes of complexing agents may be mentioned as being particularly interesting comprising: oxygen-containing tertiary amines; oxygen-containing or sulphur-containing polyethers, which can be cyclic or macrocyclic; and cryptands.

The first class consists of sequestering agents of general formula:

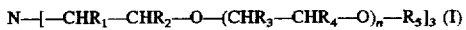

$$N—[—CHR_1—CHR_2—O—(CHR_3—CHR_4—O)_n—R_5]_3 \quad (I)$$

in which n is an integer greater than or equal to 0 and less than or equal to about 10 (0<n<10), $R_1, R_2, R_3$ and $R_4$, which may be identical or different, represent a hydrogen atom or an alkyl radical having from 1 to 4 carbon atoms and $R_5$ represents an alkyl or cycloalkyl radical having from 1 to 12 carbon atoms, a phenyl radical or a radical of formula —$C_mH_{2m}C_6H_5$, or $C_mH_{2m+1}$—$C_6H_5$, m being between 1 and about 12.

The second class of complexing agents consists of cyclic, preferably macrocyclic, polyethers having from 6 to 30 atoms in the ring and preferably from 15 to 30 atoms in the ring and consisting of 2 to 10, preferably of 4 to 10, units —O—X— in which X is either —$CHR_6$—$CHR_7$— or —$CHR_6$—$CHR_8$—$CR_9R_7$, $R_6, R_7, R_8$ and $R_9$, which may be identical or different, being a hydrogen atom or an alkyl radical having from 1 to 4 carbon atoms, it being possible for one of the Xs to be —$CHR_6$—$CHR_8$—$CR_9R_7$— when the units —O—X— comprise the group —O—$CHR_6$—$CHR_7$.

The third class of completing agents consists of the compounds described in patent application EP 0,423,008, page 3, line 29 to page 6, line 45.

Perfluorocarboxylic acid salts may advantageously be used, such as the trifluoroacetate, perfluoropropionate and perfluorobutyrate of an alkali metal, in particular potassium.

It is noted that the use of sequestering agents of the crown ether type, in solvents which are relatively non-polar (less polar than DMF), markedly accelerates the conversion of the starting fluorocarboxylic acid.

Such sequestering agents may advantageously be used in a proportion of from 5 to 100 mol %, in particular from 5 to 25 mol %, relative to their initial fluorocarboxylic acid content.

However, certain combinations with the other partners of the reaction medium, in particular certain solvents, may have a less favourable effect as regards the stability of the product formed, and will thus not be considered as being advantageous.

Another aim of the present invention is to provide a process for the synthesis of an organic derivative containing a difluoromethylene group, which uses the reagent according to the present invention.

This aim is achieved:

a) by placing the said reagent together with a compound containing at least one electrophilic function, and b) by heating the resulting mixture to a temperature of between 100° C. and 200° C., preferably of between 110° and 150° C., for a period of at least half an hour, advantageously of at least one hour, and of not more than one day, advantageously of less than 20 hours.

The placing of the reagent together with or in contact with the substrate may or may not be gradual. In particular, it is possible to wait until one of the two is at the right temperature in order to introduce the other. This introduction may or may not be gradual. The reagent may be poured into the substrate or vice versa. The fluorocarboxylate and the substrate may be introduced into the solvent both simultaneously and gradually.

The reagent of the invention reacts according to the invention with an electrophilic compound, containing an electrophilic atom, it being possible for this atom to be a carbon atom or a hetero atom, for example sulphur, selenium or tellurium. It advantageously reacts with hydrocarbon compounds on an electrophilic carbon atom not belonging to an aromatic system.

According to a first aspect of the invention, the reagent preferably reacts with compounds containing an electrophilic atom, advantageously an electrophilic hetero atom, linked to a halogen atom or to a pseudohalogen group in order to achieve the substitution of the said halogen or pseudohalogen in a single step.

The reaction works proportionately better, in contrast with an SN2 reaction, when it passes via a reaction intermediate originating from an addition onto a multiple bond or onto a doublet.

When the electrophilic atom is a sulphur atom, mention may be made of the reaction with:

- the halo or pseudohalo derivatives of organosulphur compounds, in particular sulphenyl, sulphinyl or sulphonyl halides, in which the halogen atom or the pseudohalogen group is substituted during the reaction with a substituted difluoromethyl group;
- disulphides, for example optionally substituted aryldisulphides, in which the S—S bond is broken and replaced by a substituted difluoromethyl group; suitable disulphides may in particular be $C_5$–$C_{10}$ aryl disulphides, optionally substituted with a $C_1$–$C_{10}$ alkyl, $C_1$–$C_{10}$ alkoxy or nitro group or with one or more ($\leq 3$) halogen atom(s);
- compounds of thiocyanate type in which the cyano group is substituted during the reaction with a substituted difluoromethyl group; preferred thiocyanates are $C_5$–$C_{10}$ aryl thiocyanates, including alkylaryl thiocyanates, and $C_1$–$C_{10}$ alkyl thiocyanates, including aralkyl thiocyanates.

In the above compounds, the halogen atom may be selected from iodine, bromine, chlorine and fluorine atoms. A "pseudohalogen" group is a group which, when leaving, in anionic form, has an associated acid whose pKa is less than 4, preferably less than 3, in particular less than 0.

Groups whose associated acid has an acidity (measured by the Hammett constant) at least equal to that of acetic acid, advantageously to that of sulphonic acids, or trihalo acids, are preferred. One of the typical pseudohalogens is a perfluoroalkanesulphonyloxy group which releases a perfluoroalkanesulphonate. Preferred pseudohalogen groups may be selected from the tosylate (p-toluenesulphonyloxy), mesylate (methanesulphonyloxy), trifluoromethanesulphonyloxy or trifluoroacetoxy group. The acetate group may also be considered as such a leaving group.

According to a second aspect, the reagent also reacts advantageously with a compound selected from carbonyl compounds of ketone, aldehyde, acid halide, activated ester or anhydride type, by performing an addition on the carbonyl function. Preferred and non-limiting examples which may be mentioned are aromatic aldehydes, preferably $C_5$–$C_{10}$ aldehydes, in which the aromatic ring may optionally be substituted with a $C_1$–$C_{10}$ alkyl, $C_1$–$C_{10}$ alkoxy or nitro group or with a halogen atom; cyclic ketones such as cyclohexanone; non-enolizable ketones activated with a donor group, such as trifluoromethylacetophenone; aromatic anhydrides, such as benzoic anhydride.

When there is a risk of reaction between the substrate and the fluorocarboxylate, it may then be preferable to introduce the substrate or the fluorocarboxylate only under conditions of decarboxylation of the said carboxylate (see the above implementation conditions).

The reaction product is generally an alcohol in this case (for example in alkoxide form), the carbon atom of which bearing the hydroxyl function is substituted with a substituted difluoromethyl group. This product may optionally react subsequently with the reagent or with the starting material according to the reaction conditions.

In general, the amount of reagent employed in the process of the invention will be set in a manner known per se according to the functionality of the electrophilic compound.

It should be pointed out that the product derived from the decomposition of the fluorocarboxylic acid may react with itself if it contains one of the functions liable to react, such as those mentioned above.

It may be noted that compounds, in liquid form, containing an electrophilic function are capable of being used as solvent according to the present invention, provided that they are aprotic. The reaction of the present invention may thus be advantageously performed by placing together a) a fluorocarboxylic acid salt as defined above with b) a compound containing at least one electrophilic function acting both as solvent and as reaction substrate.

When using the reagent according to the invention with a substrate containing at least one electrophilic function, it is important that the latter substrate disrupts the conditions described above as little as possible.

Thus, it is preferable to use a sufficiently dehydrated substrate, or one which neither contains acidic hydrogen which may be removed by strong bases nor contains harmful impurities, that is to say, in general, a substrate which satisfies the same constraints as those outlined for the reagent.

It has been possible to observe that, all factors being otherwise equal, the yield of the intended organic derivative depends on the degree of progress of the reaction and that a very low final yield may be obtained despite a considerable level of conversion of the reagents. Without wishing to be linked to any particular scientific theory, it appears that everything takes place as if there were formation kinetics and degradation kinetics for the products obtained.

In order to avoid an excessive degradation of the final product, and thus to ensure good selectivity of the reaction, it is preferable not to seek to convert the starting fluorocarboxylic acid completely. The progress of the reaction may be controlled by the rate conversion (RC) of the acid, which is the molar ratio of the amount of acid consumed to the initial amount of acid in the reaction medium, this rate being readily calculated after assay of the acid remaining in the medium.

Advantageously, the reaction will only be carried out until a rate of conversion of 40 to 80%, preferably of 50 to 70%, is produced, and the reaction products will then be separated. It is thus possible to achieve a selectivity of the order of 80% expressed by the desired product/converted fluorocarboxylic acid molar ratio.

In order to be within optimum reaction conditions, it is possible to limit the rate of conversion by acting at the same time on the duration of the reaction, the nature of the solvent and the presence of additives which have a tendency to limit this conversion, for example such as fluoride ions. The reaction kinetics depend, in addition, on the reaction partners (fluorocarboxylic acid and electrophilic reagent) and the appropriate reaction time may readily be adapted to each individual case as a function of these kinetics.

Once the desired rate of conversion has been achieved, the reaction mixture may be treated in a manner which is known per se in order to separate out the product obtained, it being possible for the starting materials to be recycled in order to produce an additional amount of the intended organic derivative.

An additional chemical reaction which allows the desired product to be converted into a more volatile and readily distilled derivative may, if necessary, be carried out for the separation.

The examples which follow illustrate the invention.

EXAMPLE 1

Synthesis of 1-Trifluoromethylbenzyl Alcohol

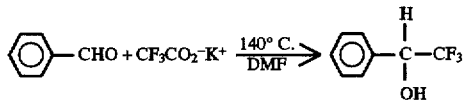

4.98 g (32.7 mmol) of potassium trifluoroacetate and 2 g (18.8 mmol) of benzaldehyde are mixed together in 26 g of anhydrous DMF, under a nitrogen atmosphere.

The molar ratio of the trifluoroacetate to the benzaldehyde is 1.7.

The mixture obtained is transferred to a 50 ml Hastelloy reactor. Once the reactor is closed, the mixture is heated at 104° C. for 3 h 30.

After cooling to 5° C., the reaction crude is drawn off, diluted in $CH_2Cl_2$ and washed with water.

The organic phase is dried and then assayed by gas chromatography.

The rate of conversion (RC) of the benzaldehyde is 50% (in terms of number of moles of benzaldehyde converted relative to the initial number of moles of benzaldehyde) and the actual yield (AY) of 1-trifluoromethylbenzyl alcohol is 20%.

EXAMPLE 2

The reaction between potassium trifluoroacetate and benzaldehyde is carried out as in Example 1, replacing the DMF by NMP (N-methylpyrrolidone).

7.6 g of $CF_3CO_2^-K^+$ (50 mmol) and 3.2 g of benzaldehyde (30 mmol) are dissolved in 40 g of NMP.

The water content of the medium is less than 4 mol % relative to the trifluoroacetate.

The mixture is heated at 140° C. for 3 h 30.

The processing and assay of the reaction crude performed as in Example 1 gives

Rate of conversion of the benzaldehyde = 55%

Yield of 1-trifluoromethylbenzyl alcohol = 15%

EXAMPLE 3

The reaction between potassium trifluoroacetate and benzaldehyde is carried out as in Example 1, the DMF being replaced by acetonitrile. 2 g of benzaldehyde and 4.75 g of potassium trifluoroacetate are dissolved in 25 ml of $CH_3CN$.

The mixture is heated at 140° C. for 3 h 30.

After processing and assay of the reaction crude, the following are obtained

Rate of conversion of the benzaldehyde = 53%

Yield of 1-trifluoromethylbenzyl alcohol = 2.5%

The main product formed in this reaction is cinnamonitrile (Z and E isomers).

Cinnamonitrile is formed by condensation of the anion of acetonitrile with benzaldehyde, followed by dehydration.

This example shows that the solvent to be used should not have excessively acidic protons.

EXAMPLE 4

The reaction between potassium trifluoroacetate (5.05 g; 32.7 mmol) and para-fluorobenzaldehyde (2.5 g; 20.2 mmol) in 25 ml of DMF is performed under the conditions of Example 1.

The mixture is heated at 140° C. for 4 h 00.

After processing, gas chromatographic (GC) assay gives

RC p-fluorobenzaldehyde = 75%

AY 1-trifluoromethyl(p-fluorobenzyl) alcohol ≦ 2%

The main product corresponds to the addition of the intermediate trifluoromethyl carbinolate formed with the para-fluorobenzaldehyde:

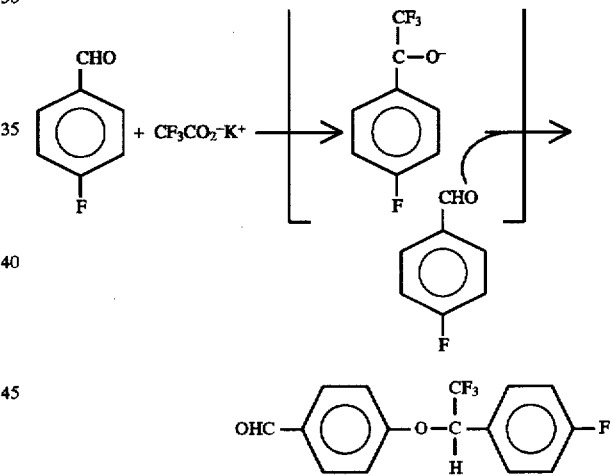

This reaction shows that when the electrophile used contains several reactive functions, side reactions may take place.

EXAMPLE 5

A mixture consisting of 1.43 g of $CF_3CO_2^-K^+$ (9.44 mmol) and 0.55 g of cyclohexanone (5.6 mmol) diluted in 6.4 g of DMF is heated at 140° C. for 5 h 30. GC analysis of the reaction crude after hydrolysis gives

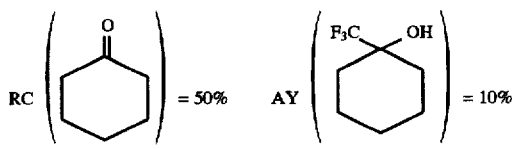

The main products formed correspond to the products of condensation of cyclohexanone with itself followed by a dehydration:

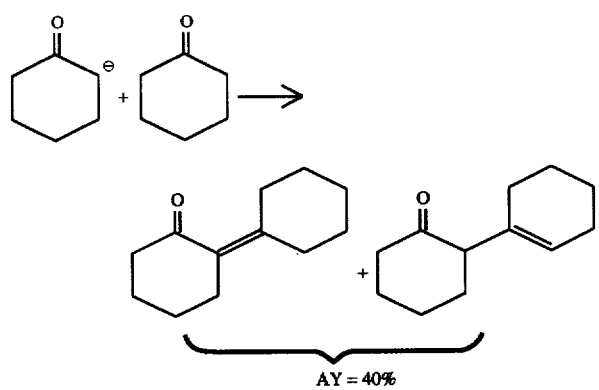

AY = 40%

This reaction snows that when the electrophile possesses an enolizable function, side reactions may take place.

EXAMPLE 6

Reaction of Trifluoromethylacetophenone with CF$_3$CO$_2$K

A mixture of CF$_3$CO$_2^-$K$^+$ (0.87 g; 5.7 mmol) and 0.62 g (3.56 mmol) of trifluoromethylacetophenone dissolved in 6.5 g of DMF is heated at 140° C. for 5 h 30.

After cooling and hydrolysis, GC analysis of the reaction medium gives

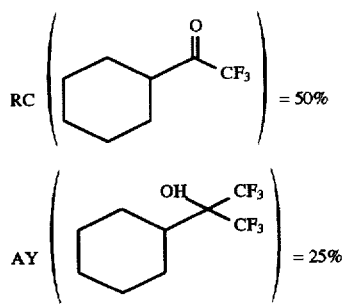

The same reaction may be performed in NMP instead of DMF.

EXAMPLE 7

Reaction Between Benzoic Anhydride and Potassium Trifluoroacetate

A mixture of 0.81 g (5.32 mmol) of CF$_3$CO$_2^-$K$^+$ and 0.7 g (3.1 mmol) of benzoic anhydride in 6.15 g of NMP is heated at 140° C. for 5 h 30. After hydrolysis, GC analysis of the reaction medium gives

RC  ((Φ-CO)$_2$O) = 100%

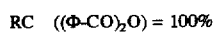

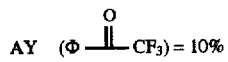

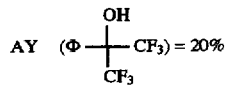

AY (Φ—C(O)—NMe$_2$) = 30%

Bis(trifluoromethyl)carbinol

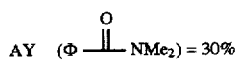

comes from the trifluoromethylation of the trifluoromethylacetophenone intermediately formed:

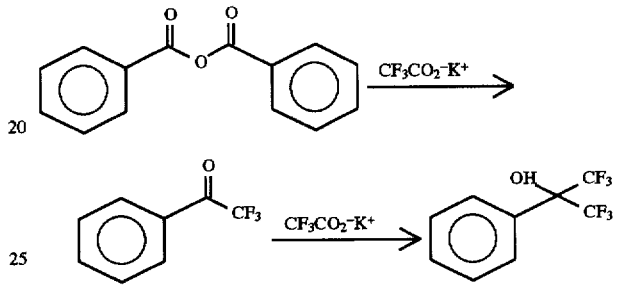

N,N-Dimethylbenzamide originates from a reaction of the degradation of DMF which produces N,N-dimethylamine, the latter reacting with benzoic anhydrides:

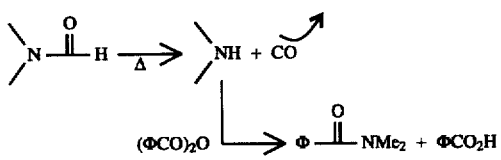

The reaction between benzoic anhydride and CF$_3$CO$_2^-$K$^+$ may also be carried out in DMF.

EXAMPLE 8

Reaction Between Diphenyl Disulphide C$_6$H$_5$SSC$_6$H$_5$ and CF$_3$CO$_2^-$K$^+$ A mixture of 0.83 g (5.46 mmol) of CF$_3$CO$_2^-$K$^+$ and 0.6 g (2.75 mmol) of diphenyl disulphide in 6.2 g of DMF is heated at 140° C. for 6 h 00.

Analysis of the reaction medium (after hydrolysis) by GC and $^{19}$F NMR gives

RC(C$_6$H$_5$SSC$_6$H$_5$)=67%

AY(C$_6$H$_5$SCF$_3$)=84%

The reaction may be carried out in the same way in NMP.

COUNTER-EXAMPLE

Working as in Example 8, but with an additional 20 mol % of CuI added relative to the initial CF$_3$CO$_2^-$K$^+$ (5.46 mmol), total inhibition of the trifluoromethylation reaction of diphenyl disulphide is obtained.

EXAMPLE 9

Reaction Between Bis(4-Nitrophenyl) Disulphide and CF$_3$CO$_2^-$K$^+$

Repeating the procedure of Example 8 with a mixture of 0.82 g (5.39 mmol) of CF$_3$CO$_2^-$K$^+$ and 0.83 g (2.7 mmol)

of bis(4-nitrophenyl) disulphide in 7 g of DMF, a reaction crude also containing, besides the starting bis(4-nitrophenyl) disulphide, 4-nitrothiofluoromethylbenzene is obtained

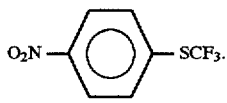

EXAMPLE 10

Reaction of benzyl thiocyanate $C_6H_5CH_2SCN$ with $CF_3CO_2^-K^+$

A mixture of 0.67 g (4.45 mmol) of $CF_3CO_2^-K^+$ and 0.42 g (2.8 mmol) of benzyl thiocyanate in 5 g of DMF is heated at 140° C. for 3 h 00.

After hydrolysis, GC analysis of the reaction crude gives:
$RC(C_6H_5-CH_2SCN)=100\%$
$AY(C_6H_5-CH_2SCF_3)=36\%$ The reaction may be carried out in a similar manner in NMP.

We claim:

1. A method for grafting a substituted difluoromethyl group onto a compound containing at least one electrophilic function, comprising:
   a) reacting said compound containing at least one electrophilic function with a reagent which comprises a fluorocarboxylic acid of formula Ew—$CF_2$—COOH where Ew represents an electron-withdrawing atom or group, at least partially salified by an organic or inorganic cation, and a polar aprotic solvent; wherein the content of releasable protons carried by the various components, including their impurities, is at most equal to half the initial molar concentration of said fluorocarboxylic acid; and
   b) isolating a compound obtained in step a) which comprises a substituted difluoromethyl group grafted thereon, wherein said compound containing at least one electrophilic function is not an aromatic compound substituted with electronegative groups.

2. The method according to claim 1, wherein said polar aprotic solvent is said compound containing at least one electrophilic function.

3. The method according to claim 1, wherein said proton content is at most equal to 10% of the initial molar concentration of said fluorocarboxylic acid salt.

4. The method according to claim 1, wherein said reagent has a water content less than 10% of the molar concentration of said fluorocarboxylic acid.

5. The method according to claim 1, wherein said reagent has a content of transition elements having at least two stable valency states less than 1000 mol ppm, relative to said fluorocarboxylic acid salt.

6. The method according to claim 1, wherein said reagent has a content of elements from column VIII of the Periodic Table of the Elements less than 100 mol ppm, relative to the fluorocarboxylic acid salt.

7. The method according to claim 1, wherein said reagent has a content, expressed as equivalents, of ionic fluoride at most equal to the initial molar concentration of said fluorocarboxylic acid salt.

8. The method according to claim 1, wherein the donor number of said polar aprotic solvent is between 10 and 30.

9. The method according to claim 1, wherein the acceptor number of said polar aprotic solvent is less than 20.

10. The method according to claim 1, wherein the pKa corresponding to the first acidity of said solvent is at least equal to 20.

11. The method according to claim 1, wherein said reagent comprises a sequestering crown ether.

12. The method according to claim 1, wherein said electron-withdrawing atom or group is an electron-withdrawing group whose Hammet constant $\sigma_p$ is at least equal to 1.

13. The method according to claim 1, wherein said acid is a compound of formula (1) X—$CF_2$—COOH, where X represents a halogen atom; or a compound of formula (2) R—G—$CF_2$—COOH, where R—G represents a nitrile group or alternatively G represents >C=O, >S=O or —$(CF_2)_n$— with n greater than or equal to 1 and R represents, without discrimination, an organic or inorganic residue.

14. The method according to claim 1, wherein said fluorocarboxylic acid or acid salt is fully soluble in the reagent medium.

15. The method according to claim 1, wherein said acid salt is a salt of an alkali metal, said metal being sodium, potassium, rubidium, caesium or francium; or a quaternary ammonium salt.

16. The method according to claim 1, wherein the solvents are N-disubstituted amides, cyclic or acyclic ethers or benzonitrile.

17. A method for grafting a substituted difluoromethyl group onto a compound containing at least one electrophilic function, comprising:
   a) reacting the compound containing at least one electrophilic function with a reagent which comprises a fluorocarboxylic acid of formula Ew—$CF_2$—COOH where Ew represents an electron-withdrawing atom or group, at least partially salified by an organic or inorganic cation, and a polar aprotic solvent; wherein the content of releasable protons carried by the various components, including their impurities, is at most equal to half the initial molar concentration of said fluorocarboxylic acid;
   b) heating the resulting mixture at a temperature of between 100° C. and 200° C., for a period of between ½ hour and one day; and
   c) isolating the compound containing at least one electrophilic function obtained thereby; wherein said compound containing at least one electrophilic function is not an aromatic compound substituted with electronegative groups.

18. A method for grafting a substituted difluoromethyl group onto a compound containing at least one electrophilic function, comprising:
   a) reacting the compound containing at least one electrophilic function with a reagent which comprises a fluorocarboxylic acid of formula Ew—$CF_2$—COOH where Ew represents an electron-withdrawing atom or group, at least partially salified by an organic or inorganic cation, and a polar aprotic solvent; wherein the content of releasable protons carried by the various components, including their impurities, is at most equal to half the initial molar concentration of the said fluorocarboxylic acid;
   b) heating the resulting mixture at a temperature of between 100° C. and 200° C., for a period of between ½ hour and one day; and
   c) isolating the compound containing at least one electrophilic function obtained thereby; wherein said compound containing an electrophilic function is selected from halo or pseudohalo derivatives of organosulphur compounds, disulphides, thiocyanates, and carbonylated compounds; wherein said compound containing at least one electrophilic function is not an aromatic compound substituted with electronegative groups.

19. The method according to claim 18, wherein said compound containing an electrophilic function is selected from a sulphenyl, sulphinyl or sulphonyl halide, a ketone, an aldehyde, an acid halide, an activated ester or an anhydride.

20. The method according to claim 17, wherein said compound contains at least one electrophilic function not containing any hydrogen which can be removed by a strong base.

* * * * *